United States Patent
Halden et al.

(12)

(10) Patent No.: US 6,326,049 B1
(45) Date of Patent: Dec. 4, 2001

(54) PASTA MANUFACTURING PROCESS

(75) Inventors: Jonas Peter Halden, Seuzach; Annabella Realini, Lutry; Marcel Alexandre Juillerat, Lausanne; Carl Erik Hansen, Epalinges, all of (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/453,942

(22) Filed: May 24, 2000

(30) Foreign Application Priority Data

Jun. 4, 1999 (EP) .................................................. 99201763

(51) Int. Cl.$^7$ ........................................................ A23L 1/16
(52) U.S. Cl. ............................................. 426/557; 426/451
(58) Field of Search ...................................... 426/557, 451

(56) References Cited

U.S. PATENT DOCUMENTS 3,520,702  7/1970  Menzi ...................................... 99/85

FOREIGN PATENT DOCUMENTS 09 070269 A  2/1980  (JP) .

*Primary Examiner*—Lien Tran

(57) ABSTRACT

A pasta having a reduced residual lipase activity, a long shelf life, and the ability to retain of its characteristic yellow color over time. This pasta may be manufactured by preparing a mixture comprising a cereal flour or semolina, water, and lipase; kneading the mixture into a dough; and forming the dough into a pasta, with the steps being conducted to provide a residual lipase activity of the pasta which is lower than about 100 LU/kg pasta. A heat treatment of the dough can be utilized to help achieve the desired reduction in lipase activity.

10 Claims, No Drawings

PASTA MANUFACTURING PROCESS

CROSS-REFERENCE TO RELATED APPLICATIONS

Not Applicable

STATEMENT REGARDING FEDERALLY SPONSORED RESEARCH

Not Applicable

REFERENCE TO A MICROFICHE APPENDIX

Not Applicable

FIELD OF THE INVENTION

The present invention relates to a pasta that has a reduced residual lipase activity. This pasta may be manufactured by preparing a mixture comprising a cereal flour or semolina, water, and lipase; kneading the mixture into a dough; and forming the dough into a pasta, with the steps being conducted to provide a residual lipase activity of the pasta which is lower than about 100 LU/kg pasta.

BACKGROUND OF THE INVENTION

U.S. Pat. No. 3,520,702 to Menzi discloses a method of making dried pasta from semolina and water, which comprises adding to either the semolina or the water a small amount of enzymatic substance, such as pancreatin, glucose-oxidase, catalase, proteinase, amylase, or wheat germ lipase, preparing a paste from semolina and water, kneading, extruding and drying, the pasta thus obtained being highly resistant to cooking so that, once cooked, it has a very good elasticity and is not sticky.

Japanese Patent No. JP-09-070269A to Nisshin Flour Milling Co. discloses a process for manufacturing noodles, which comprises adding water, salt, oil, and lipase to wheat flour or other cereal grain flour, kneading to form a dough, allowing the dough to rest at room temperature to mature it, and using the dough for making noodles in fresh, semi-dried, or dried form.

SUMMARY OF THE INVENTION

The present invention is directed to a pasta having a residual lipase activity after manufacture of less than about 100 LU/kg pasta, and to a process for making such pasta. The process includes the steps of: preparing a mixture comprising a cereal flour or semolina, water, and lipase; kneading the mixture into a dough; and forming the dough into a pasta, such that the residual lipase activity of the pasta ends up being less than about 100 LU/kg pasta, preferably less than about 50 LU/kg pasta. Advantageously, the process can further include conducting a heat treatment step to assist in achieving the residual lipase activity.

In one embodiment, the pasta is formed by extrusion. In a preferred embodiment, the heat treatment may be conducted after forming the pasta. This heat treatment may optionally include drying the pasta, preferably at a temperature from about 84° C. to about 100° C. and preferably for a period of time from about 200 to about 700 minutes. Alternatively, the pasta can be at least partially dried.

In another preferred embodiment, the heat treatment may be conducted after the extrusion step by one or more of blanching or cooking, preferably by blanching. Preferably, the blanching can be conducted at about 85° C. to about 100° C. for about 1 minute to about 10 minutes, while steaming with steam at about 98° C. to about 100° C. and spraying water at about 85° C. to about 98° C.

Advantageously, $CO_2$ in gaseous form may be introduced into the mixture, advantageously before the kneading step, to help preserve the color of the pasta.

The pasta itself can be processed from a dough comprising cereal flour or semolina, water, and lipase, for example, by a process such as listed above. This pasta has a reduced lipase activity lower than about 100 LU/kg pasta, and preferably lower than about 50 LU/kg pasta. Advantageously, the pasta may possess no noticeable rancidity after at least one year of storage, preferably after at least two years of storage. Optionally, the residual lipase activity of the pasta can be lowered by subjecting the pasta to heat treatment. Additionally, the pasta may be formed by extrusion.

BRIEF DESCRIPTION OF THE SEVERAL VIEWS OF THE DRAWINGS

Not Applicable

DETAILED DESCRIPTION OF THE PREFERRED EMBODIMENTS

Throughout the present description and claims the expression "lipase activity left in the pasta" means "lipase activity within the pasta as measured immediately after its manufacture."

One aspect of the present invention is to provide a pasta that has a reduction in the residual lipase activity, and preferably so that practically no lipase activity is left in the pasta. Another aspect of the present invention is to provide a pasta which has a long shelf life, namely in which practically no rancidity may be noticed after one to two years storage from about 15° C. to about 30° C. in a traditional cellophane package. Yet another aspect of the present invention is to provide a pasta in which its original yellow color is preserved.

To this end, the present pasta may be manufactured by a process consisting of preparing a mixture comprising a cereal flour or semolina, water, and lipase, kneading the mixture into a dough, and forming the dough into a pasta shape, such that the residual lipase activity left in the pasta is lower than about 100 LU/kg pasta, preferably lower than about 50 LU/kg pasta. If desired, the reduced lipase activity can be achieved by conducting a heat treatment on the dough that is used to make the pasta. It has surprisingly been found that it is possible in this way to obtain the known advantages of pasta made by a process aided by the use of lipase. Such pasta has an improved texture, especially an improved firmness, and is not sticky, while reducing the activity of lipase in the finished product to levels sufficient to avoid rancidity in the pasta product, especially after one to two years storage.

To implement the present process for manufacturing pasta, a mixture of cereal flour or semolina, water, and lipase may be prepared, for example, having a water content from about 25% to about 40%. The cereal flour or semolina may be Durum or hard wheat semolina, the quality of which need not be premium, or even soft wheat flour, for example. The mixture may contain lipase in an amount from about 500 to about 50,000 Lipase Units (LU) per kg of cereal flour or semolina, for example. The lipase may be any food grade lipase available on the market, for example, such as the enzyme sold under the name Lipopan 50 BG by the Danish company NOVO NORDISK or the enzyme sold under the name GRINDAMYL EXEL 16 by the Danish company DANISCO. The mixture may further include additives, for example, such as egg material, sodium chloride, spices, antioxidants, and/or emulsifiers.

Egg material in the form of whole egg powder, egg white powder or liquid whole egg may be added to the mixture in order to further increase the firmness of the pasta, a main contribution to such an increase being indeed already obtained by using lipase, for example. The mixture may be prepared in the form of a premix of dry or powdery ingredients to which water is added, for example. Lipase may be incorporated into the premix or into a portion of the water, for example. In this regard, it has surprisingly been found that an effective preservation of the color may be obtained if $CO_2$ in gaseous form is injected into the mixture, for example, during kneading.

The mixture may be prepared, kneaded, and formed in any known pasta making way, especially using equipment, such as a paddle mixer, a twin screw kneader and a single screw extruder, a twin screw mixer-kneader and a single screw extruder, a twin screw mixer-kneader-extruder, or a twin screw mixer-kneader assisted by a gear pump for the extrusion, for example. Care should be taken to ensure that the temperature of the mixture during mixing, kneading, or extrusion remains below 55° C.

An extruded pasta may be cut into long pasta goods such as long spaghetti, or into short pasta goods such as short spaghetti, linguine, eliche, or macaroni, for example.

In a first preferred embodiment of the present process, where the pasta is dried after extrusion, the lipase activity may be reduced by a heat treatment that is conducted during drying at a temperature from about 84° C. to about 95° C. for about 200 to about 700 minutes. It has surprisingly been found that such a heat treatment permits reduction in the residual lipase activity of the pasta to lower than about 100 LU/kg pasta, or even lower than about 50 LU/kg pasta.

In another preferred embodiment of the present invention, where the pasta is not dried, is only partially dried, or is dried at a later stage, the heat treatment to reduce the lipase activity may be conducted by blanching and/or cooking after extrusion. In this other preferred embodiment, the extruded pasta may be hot air treated to fix the shape before blanching and to produce a product that is firmer in bite. The extruded pasta may be blanched by steaming or by hot water-spraying and steaming, for example, the purpose of water-spraying during steaming being to minimize starch losses during blanching. The blanching step may be conducted at about 85° C. to about 100° C. for about 1 minute to about 10 minutes, with or without steaming with steam at a temperature from about 98° C. to about 100° C. and, optionally, by spraying water at a temperature from about 85° C. to about 98° C., for example. The water used for spraying may be acidified water, or may contain an acid, such that the pH of the resulting solution can be from about 5.0 to about 5.8, for example. During blanching, the water uptake may be such that the blanched pasta has a total water content from about 60% to about 75%, for example. The blanching step may then be stopped by water cooling, for example. Preferably, the blanching step is followed by drying in order to obtain instant or quick cooking pasta. This drying after blanching may comprise a pre-drying step and a final drying step.

A pre-drying step, intended for reducing the water content of the blanched pasta down to between about 8% and about 13%, may be conducted at a temperature from about 85° C. to about 95° C., preferably for about 15 minutes to about 25 minutes. A final drying step, intended to stabilize the pasta to an end water content from about 4% to about 7%, may be conducted at a temperature from about 75° C. to about 98° C., preferably for about 40 minutes to about 80 minutes. It has been found that it is possible in this way to prepare, with relatively low cooking loss, pasta which is not sticky after blanching and which rehydrates or cooks relatively quickly, while maintaining a desirable color and texture (good bite). Moreover, to achieve these features, it may be desirable to effect a relatively high reduction in egg content and a relatively widespread replacement of semolina with soft wheat flour, as compared with similar pasta made without using lipase in a similar manufacturing process.

In the present process, especially in both the first and second preferred embodiments, adequate temperatures and times for lipase to develop its beneficial effect on flour or semolina and/or on the dough may be encountered during the per se traditional steps of preparing a premix and/or the mixture, e.g., kneading the mixture and forming it into a pasta shape. If needed, however, an additional maturing step may be provided before or after kneading the mixture into a dough, preferably at a temperature from about 20° C. to about 54° C. and preferably for about 30 minutes to about 180 minutes, or even before making the mixture, by simply adding the lipase to the semolina or flour and allowing them to rest at about 15° C. to about 30° C., preferably for a time period of about 3 hours to about 20 days.

EXAMPLES

The pasta and the process according to the present invention are illustrated in the following Examples in which the percentages and parts are by weight and the lipase activity is expressed and was measured according to the method disclosed hereafter.

Lipase in Pasta—radioisotope Assay with $^{14}C$-labeled Triolein-substrate:

The use of radiolabeled triacylglycerol (TAG) substrate permits specific and sensitive determination of TAG-lipase activity. The radiolabeled lipid products, produced during hydrolysis, can be separated by thin layer chromatography (TLC) and quantified by radioscanning.

Lipid Standards for Thin Layer Chromatography:

The lipids were purchased from Avanti Polar Lipids Inc. (700 Industrial Park Drive, Alabaster, AL 35007, USA), and 5 $\mu g$ of each neutral lipid (triolein, diolein, olein and oleic acid) were applied as TLC standards. The neutral lipids were prepared as 0.2 mg/ml standard solution in hexane.

Substrate:

The assay is conducted by adding labeled triolein-substrate to the cold triolein. The radiolabeled substrate is triolein (carboxyl-$^{14}C$), (NEC-674, NEN Research Products, DuPont, Wilmington, Del., USA). The cold substrate is triolein (99% pure) from Sigma (T-7140).

Emulsion (final 50 mM triolein):

1 $\mu L$ $^{14}C$-triolein (0.1 mCi/ml) per assay

Evaporate to dryness with $N_2$

Cold triolein (final 50 mM)

100 mM Bis-Tris-Cl, pH 7.0, 5% gum arabic

The emulsion is prepared with a Braun Labsonic U sonicator (Braun Diessel Biotech GmbH, Melsungen, Germany) for 60 sec at 50 Hz.

Enzyme Extract:

Spaghetti (10 g) is ground to fine powder in an IKA Universal Laboratory Mill with cooling. The powder (2 g) is homogenized in 20 ml of water using Polytron, followed by centrifugation at 5.000 g for 5 minutes. The supernatant is used for determination of enzyme activity. Alternatively, activity can be analyzed in crude suspension.

Assay:

The assay is started by adding 80 μL freshly prepared emulsion to 20 μL enzyme extract, followed by incubation for 15 to 1440 minutes at 30° C. If the experiment lasts longer than 3 h, 0.01% $NaN_3$ needs to be added.

Then, rapid mixing with 200 μL chloroform:methanol (1:1) is followed by centrifugation for phase separation. Lipase activity is determined by analyzing the organic phase for radiolabeled free fatty acids (FFA). The neutral lipids (triacylglycerol, diacylglycerol, acylglycerol and free fatty acids) are separated on high performance TLC (HPTLC) pre-coated silica gel 60 plates (100×200 mm) with toluene-:hexane:formic acid (70:30:0.5) and air-dried. This is followed by a second elution with hexane:diethyl ether:formic acid (60:40:1). The plates are air-dried again, and the lipids are stained by dipping the samples in a solution of 1.56% $CuSO_4$ in 1.2 $MH_3PO_4$, followed by charring at 180° C. for approximately 1 minute. Lipids are identified by comparing the HPTLC retention coefficients of known standards with the radioactivity in each spot and quantified with a Berthold LB 235 Tracemaster, automatic radioactivity TLC analyzer (Lab. Berthold, Wildbad, West Germany). Lipase activity is expressed as units/g fr w (μmol FFA released/min/g fr w) or, if multiplied by 1000, as LU/kg. The lowest activity which can be detected by this method is about 50 LU/kg.

Example 1

Preparation Process for Dried Spaghetti Having a Residual Lipase Activity Less Than 50 LU/kg Pasta in the form of dried spaghetti was manufactured in a traditional Bühler pasta manufacturing equipment, from a mixture having a water content of about 32% and comprising about 76% Durum semolina into which lipase (Lipopan 50 BG) was mixed at a rate of about 5,000 LU/kg, and about 24% soft water. Lipase was first pre-mixed with semolina during approximately 20 minutes before being fed to a dosing unit of the Bühler line. Water and semolina were then continuously dosed into a pre-mixing screw, mixed for about 20 minutes in a mixer and subsequently fed into a vacuum screw prior to extrusion. The dough had a temperature of about 30° C. to about 35° C. when it entered a final extruder screw. Kneading and shearing induced by the extruder screw increased the temperature to about 45° C. to about 50° C. and the pressure to about 120 bar to about 140 bar in front of an extrusion die having circular openings approximately 1.85 mm in diameter.

The extruded spaghetti was hung up on hooks, cut into proper lengths, and finally fed to drying chambers. During the drying cycle the temperature was raised to about 88° C. in about 50 minutes, maintained between about 88° C. and about 95° C. for about 97 minutes, maintained between about 84° C. and about 86° C. for about 145 minutes and cooled to about 30° C. in about 14 minutes. The spaghetti had a residual lipase activity lower than about 50 LU/kg. They were then packed and stored at around 25° C. For comparison, traditional spaghetti was manufactured in a similar way, except that no lipase was used.

Firmness measurements, stickiness measurements, and panel sensory tests were conducted for both the pasta according to the invention and the traditional one, i.e., with and without added lipase. The pasta of the invention was found to be significantly firmer and less sticky than the traditional one. The pasta maintained these properties for one year, stored at 25° C., after which the pasta of the invention was found not to be rancid at all.

Example 2

Preparation Process for Instant Macaroni Having a Residual Lipase Activity Less Than 50 LU/kg Pasta in the form of instant macaroni was manufactured in an equipment comprising a traditional Bühler pasta manufacturing equipment, a steam/water blancher and an air dryer, from a mixture having a water content of about 27.2% and comprising Durum semolina, powdered whole dry egg (around 5%, calculated on semolina), emulsifier (around 1% Dimodan, from Danisko, calculated on semolina), lipase (about 25,000 LU Lipopan 50 BG per kg of semolina), and soft water. Lipase was first pre-mixed with about 10% of the semolina and left to stand for approximately 6.5 hours before being mixed with egg, water, and a solution of Dimodan. The mixture was kneaded and extruded under conditions similar to the conditions illustrated in Example 1, although an extrusion die having adequate openings for obtaining macaroni was used instead of one for spaghetti.

The extruded macaroni were blanched in the steam/water blancher at about 90° C. for around 6 minutes while steaming with steam at about 99° C. and spraying acidified water (pH about 5.5) at about 85° C. The macaroni had a water content of around 62.3% after blanching. The blanched macaroni was then pre-dried at about 85° C. to about 91° C. for about 28 minutes down to a water content from about 11% to about 13%. The pre-dried macaroni was finally dried at approximately 78° C. for about 90 minutes down to a residual water content of about 6%, and chilled. The instant macaroni thus obtained had a residual lipase activity lower than about 50 LU/kg. It was then packed and stored at around 25° C.

After reconstitution by simply pouring hot water over them, the macaroni had a nice yellow color, a good bite, and was not sticky. The pasta maintained these properties for one year, stored at 25° C., after which the pasta of the invention was found not to be rancid at all.

Example 3

Alternative Preparation Process for Instant Macaroni Having a Residual Lipase Activity Less Than 50 LU/kg Pasta in the form of instant macaroni was manufactured in equipment comprising a traditional Bühler pasta manufacturing equipment, a steam/water blancher and an air dryer, from a mixture having a water content of about 29.0% and comprising approximately equal amounts of Durum semolina and soft wheat flour, powdered whole dry egg (about 10%, calculated on semolina plus soft wheat flour), emulsifier (about 1% Dimodan, from Danisko, calculated on semolina plus soft wheat flour), lipase (about 25,000 LU Lipopan 50 BG per kg of semolina plus soft wheat flour) and added soft water. Lipase was first pre-mixed with around 10% of the semolina plus soft wheat flour and left to stand for about 7 days before being mixed with egg, water and a solution of Dimodan. The mixture was kneaded and extruded under conditions similar to the conditions illustrated in Example 1, although an extrusion die having adequate openings for obtaining macaroni was used instead of one for spaghetti.

The extruded macaroni was blanched in the steam/water blancher at about 90° C. for around 6 minutes while steaming steam at about 99° C. and spraying acidified water (pH around 5.5) at about 85° C. The macaroni had a water content of about 63.4% after blanching. The blanched macaroni was then pre-dried at about 85° C. to about 91° C. for around 28 minutes down to a water content from about 11% to about 13%. The pre-dried macaroni was finally dried at approximately 78° C. for about 90 minutes down to a residual water content of around 6%, and chilled. The instant macaroni thus obtained had a residual lipase activity lower than about 50 LU/kg. It was then packed and stored at around 25° C.

After reconstitution by simply pouring hot water over the pasta, the macaroni had a nice color, a good bite, and was not sticky. The pasta maintained these properties for one year, stored at 25° C., after which the pasta of the invention was found not to be rancid at all.

Example 4

Alternative Preparation Process for Instant Macaroni Having a Residual Lipase Activity Less Than 50 LU/kg Instant macaroni was prepared in the way illustrated in Example 2, except for the fact that lipase was first pre-mixed with about 10% of the water. The remaining part of water was added, followed by combination with a mixture of egg, a solution of Dimodan, and the semolina. The instant macaroni thus obtained had qualities very similar to those of the pasta of Example 2.

Deposit of computer program listings

Not applicable

What is claimed is:

1. A process for manufacturing pasta which comprises:
preparing a mixture comprising a cereal flour or semolina, water and lipase;
kneading the mixture into a dough;
forming the dough into a pasta; and
heat treating the pasta by blanching the pasta at about 85° C. to about 100° C. for about 1 to about 10 minutes while steaming the pasta with steam at about 98° C. to about 100° C. and spraying water on the pasta at about 85° C. to about 98° C. to provide a pasta having a residual lipase activity which is lower than about 100 LU/kg pasta.

2. The process of claim 1 wherein the residual lipase activity of the pasta is less than about 50 LU/kg pasta.

3. The process of claim 1, wherein the pasta is formed by extrusion.

4. The process of claim 1 wherein the water that is sprayed on the pasta has a pH of from about 5 to about 5.8.

5. The process of claim 4 which further comprises treating the pasta with hot air before blanching to fix its shape.

6. The process of claim 4 wherein the pasta has a water content of about 60% to about 75% by weight after heat treating, and which further comprises drying the pasta to a final water content of about 4% to about 7% by weight.

7. The process of claim 6 wherein the heat-treated pasta is pre-dried to a water content of about 8% to about 13% by weight by heating the pasta at a temperature of about 85° C. to 95° C. for a time of about 15 to about 25 minutes, followed by further drying of the pasta to the final water content by heating to a temperature of about 75° C. to 98° C. for a time of about 40 to about 80 minutes.

8. The process of claim 1 which further comprises maturing the dough prior to heat treating by holding the mixture for between about 20° C. and 54° C. for about 30 to about 180 minutes.

9. The process of claim 1 which further comprises maturing the dough prior to heat treating by adding the lipase to the cereal flour or semolina to form a mixture and holding the mixture at about 15° C. and 30° C. for about 3 hours to about 20 days.

10. The process of claim 1 further including the introduction of $CO_2$ in gaseous form into the mixture before kneading in an amount sufficient to help preserve the color of the pasta.

* * * * *